(12) United States Patent
Silcott et al.

(10) Patent No.: US 7,106,442 B2
(45) Date of Patent: Sep. 12, 2006

(54) MULTI-SPECTRAL OPTICAL METHOD AND SYSTEM FOR DETECTING AND CLASSIFYING BIOLOGICAL AND NON-BIOLOGICAL PARTICLES

(76) Inventors: David B. Silcott, 1135 Saffell Rd., Reisterstown, MD (US) 21136; Alexander J. Fielding, 2846 Westminster St., Manchester, MD (US) 21102

( * ) Notice: Subject to any disclaimer, the term of this patent is extended or adjusted under 35 U.S.C. 154(b) by 246 days.

(21) Appl. No.: 10/834,537

(22) Filed: Apr. 29, 2004

(65) Prior Publication Data
US 2005/0243307 A1 Nov. 3, 2005

(51) Int. Cl.
*G01N 15/02* (2006.01)
*G01N 21/00* (2006.01)
(52) U.S. Cl. .................. 356/338; 356/336; 356/343
(58) Field of Classification Search .............. None
See application file for complete search history.

(56) References Cited

U.S. PATENT DOCUMENTS

| | | | |
|---|---|---|---|
| 3,470,373 A | 9/1969 | Brewer et al. | |
| 3,566,114 A | 2/1971 | Brewer | |
| 4,548,500 A | 10/1985 | Wyatt et al. | |
| 4,651,010 A | 3/1987 | Javan | |
| 4,679,939 A | 7/1987 | Curry et al. | |
| 5,123,731 A | 6/1992 | Yoshinaga et al. | |
| 5,474,910 A | 12/1995 | Alfano | |
| 5,619,324 A | 4/1997 | Harvill et al. | |
| 5,701,012 A | 12/1997 | Ho | |
| 5,895,922 A * | 4/1999 | Ho | 250/492.1 |
| 5,999,250 A * | 12/1999 | Hairston et al. | 356/73 |
| 6,040,574 A | 3/2000 | Jayne et al. | |
| 6,118,531 A | 9/2000 | Hertel et al. | |
| 6,194,731 B1 | 2/2001 | Jeys et al. | |
| 6,490,530 B1 * | 12/2002 | Wyatt | 702/24 |
| 6,532,067 B1 * | 3/2003 | Chang et al. | 356/318 |
| 2003/0098422 A1* | 5/2003 | Silcott et al. | 250/458.1 |
| 2003/0232445 A1* | 12/2003 | Fulghum, Jr. | 436/63 |
| 2005/0024641 A1 | 2/2005 | DeFreez et al. | |

FOREIGN PATENT DOCUMENTS

EP 1 158 292 A 11/2001

OTHER PUBLICATIONS

Wyatt, "Some chemical, physical, and optical properties of fly ash particles," Applied Optics, vol. 19, No. 6, pp. 975-983 (Mar. 15, 1980).
Steinkamp et al., "Improved multilaser/miltiparameter flow cytometer for analysis and sorting of cells and particles," Rev. Scientific Instruments, American Inst. Of Physics, vol. 62, No. 11, pp. 2751-2764 (Nov. 1, 1991).
Green et al., "Flow cytomeric determination of size and complex refractive index for marine particles: comparison with independent and bulk estimates," Applied Optics, vol. 42, No. 3, pp. 526-541 (Jan. 20, 2003).
Szymanski et al., "A new method for the simultaneous measurement of aerosol particle size, complex refractive index and particle density," Measurement Science and Technology, vol. 13, No. 3, pp. 303-307 (Mar. 2002).

(Continued)

*Primary Examiner*—Michael P. Stafira
(74) *Attorney, Agent, or Firm*—Kilpatrick Stockholm LLP; David M. Krasnow

(57) ABSTRACT

Enhanced methods, apparatuses and systems are disclosed for the real-time detection and classification of biological and non-biological particles by substantially simultaneously measuring a single particle's characteristics in terms of size and density, elastic scattering properties, and absorption and fluorescence.

58 Claims, 16 Drawing Sheets

OTHER PUBLICATIONS

Wyatt et al., "A new instrument for the study of individual aerosol particles, "J. Colloid and Interface Science, vol. 39, No. 1, pp. 125-135 (Apr. 1972).

Molva, "Microchip lasers and their applications in optical Microsystems," Optical Materials, vol. 11, No. 2-3, pp. 289-299 (Jan. 1999).

* cited by examiner

Figure 2a Randomly Sampled Indoor Aerosol Particle
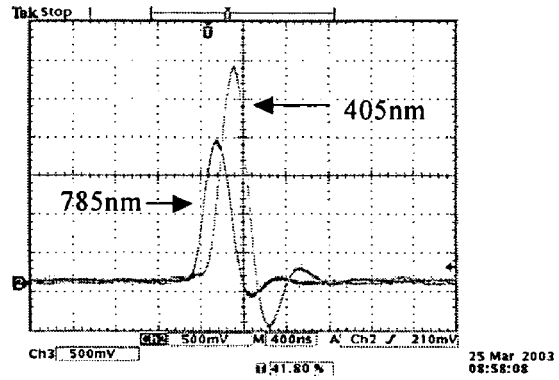
Figure 2b Randomly Sampled Indoor Aerosol Particle
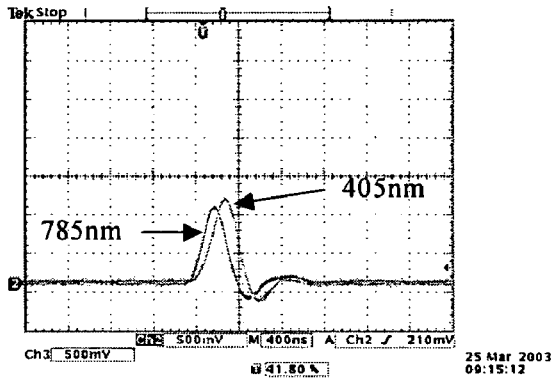
Figure 2c Randomly Sampled Indoor Aerosol Particle
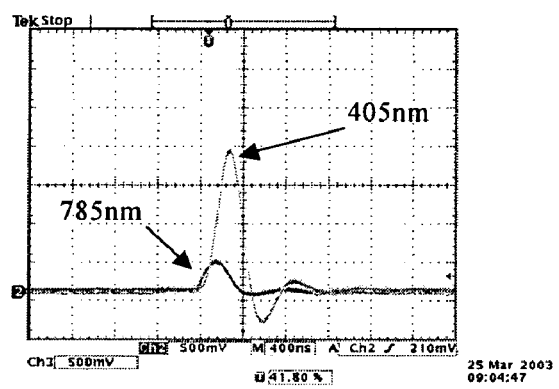
Figure 2d Randomly Sampled Indoor Aerosol Particle
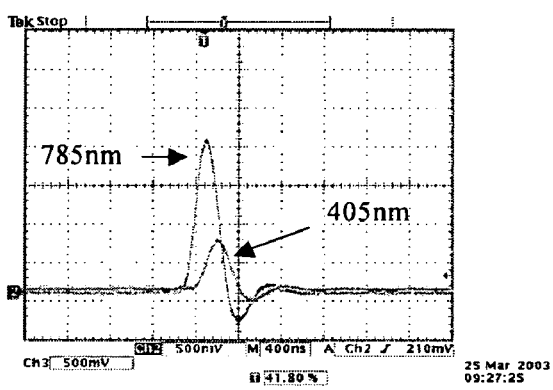
Figure 2e Randomly Sampled Indoor Aerosol Particle
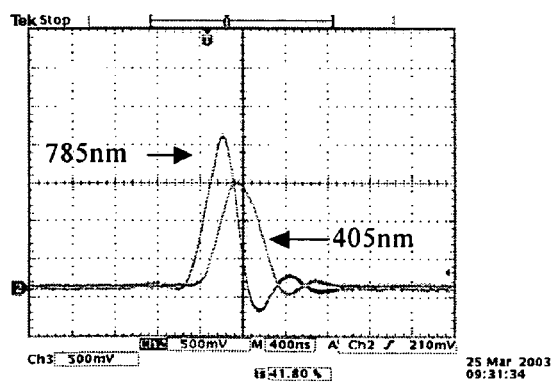
Figure 2f Randomly Sampled Indoor Aerosol Particle
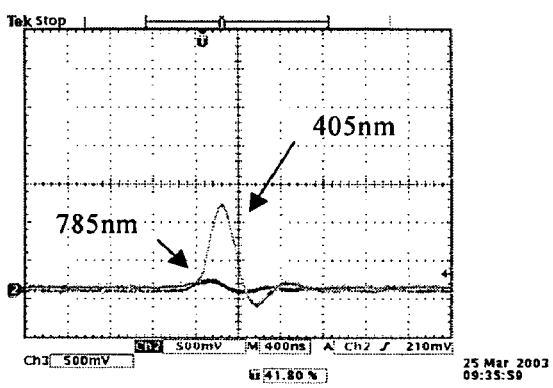

Figure 3a  BG Spore
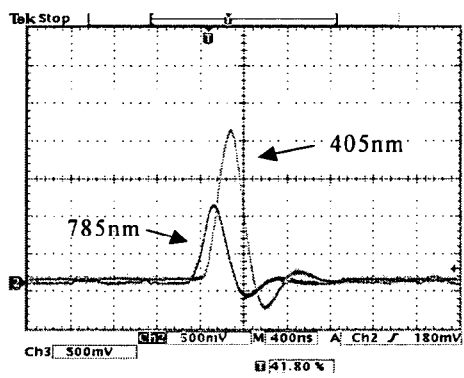
Figure 3b  Two BG Spore Events
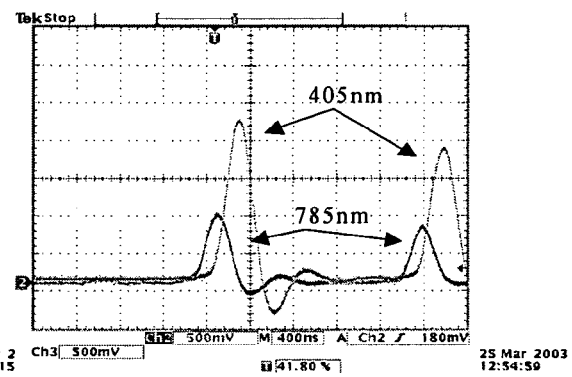
Figure 3c  0.7u PSL Particle
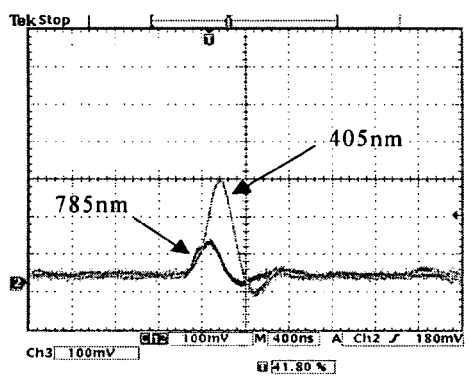
Figure 3d  1.0u Fluorescent
PSL Particle
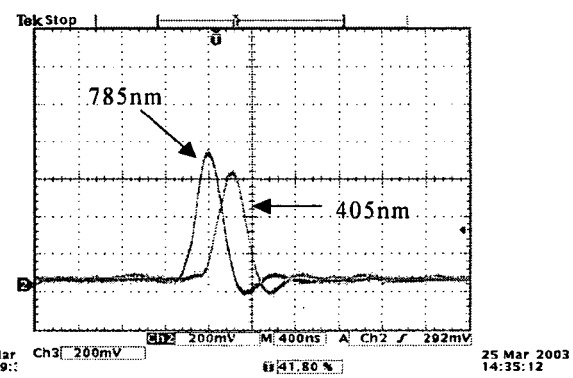

MULTI-SPECTRAL OPTICAL METHOD AND SYSTEM FOR DETECTING AND CLASSIFYING BIOLOGICAL AND NON-BIOLOGICAL PARTICLES

CROSS-REFERENCE

This application claims the benefit of U.S. Provisional Patent Application No. 60/446,042, filed Apr. 29, 2003.

FIELD OF INVENTION

This invention pertains generally to aerosol analyzers and more specifically to multi-spectral optical analyzers for the real-time detection and classification of biological and non-biological particles.

BACKGROUND OF THE INVENTION

There is a growing need for the real-time detection and classification of airborne biological and non-biological particles for indoor and outdoor air quality monitoring, as well as, for the early detection of deliberate releases of biological agent aerosols on the battlefield and in urban environments, such as through a terrorist act. Airborne microorganisms can cause diseases and the real-time monitoring of hospitals, manufacturing operations, sewage plants, animal production houses, and recycling or composting plants can help prevent harmful exposure of microorganisms in these environments. Further detection of particle-sized impurities can benefit quality and production, for example, in chip manufacturing processes. There is a further need to monitor the exposure of humans to organic carbon particulates in urban environments. The majority of organic carbon particulates encountered in the environment from such sources as diesel emissions and burning vegetation contain polycyclic aromatic hydrocarbons which are carcinogenic to humans.

The ability to provide a real-time warning of a bio-aerosol attack is a challenging problem. Present state-of-the-art real-time biological point detection involves sensing the auto-fluorescence of biological particulates via the excitation of endogenous fluorophores and by measuring the elastic scattering of particles. There are two primary limitations of the present art. First, is the inability to sense in a reliable manner low levels of cellular and spore type particles in singlet form and protein toxin and viral aggregates that fall below a stated level, e.g. a couple of microns. Second, is the inability to classify biological particles in a manner that produces a low false alarm rate when set for a threat level that corresponds to a low-level attack.

The recent delivery of parcels containing weapons-grade Anthrax, or other biological particles, and the release of these spores into the U.S. postal system demonstrated a spore-type threat delivered primarily in singlet form. Other potential attacks related to terrorist activity could be the release of biological agents into public areas, facilities and government complexes. The dispersal methods employed would determine in what form the biological agent would be packaged. In other words, the dispersal methods employed would determine what size aggregate was generated, or if single cellular or spore-type agents were generated.

For example, with a crop duster or portable crop sprayer, one could assume that a respirable range of aggregates larger than a two to ten (2–10) micron in diameter would be the predominant size generated primarily because of the water droplet diameter that these types of atomizers produce. However, for a covert release in a facility or public area, one could expect a dry powder release or a low output nebulizer could be used that would generate cellular and spore-type agents in single form or viral/protein toxin aggregates that are below 1 micron in size.

U.S. Patent Application Publication No. U.S. 2003/0098422 A1 discloses a method and apparatus for biological particle detection and classification using Mie scattering techniques and auto-fluorescence. Such Application is incorporated by reference in its entirety as if made a part of this present application.

In preparing for all threat scenarios, the ability to detect small viral/protein toxin aggregates and the singlet form of cellular and spore-type agents is required, in addition to, the conventional respirable range aggregate (2–10 micron). A further requirement is the ability to classify biological agents of interest and to separate them from commonly encountered biological particulates such as mold spores, pollens, and other biological cells and spores, as well as, other types of commonly encountered aerosols such as diesel soot and inorganic/organic particulates. Efforts directed at classification of most types of aerosols commonly encountered, as well as the biological agents of interest, will have a direct impact on the false alarm rate of real-time biological agent detection.

SUMMARY OF THE INVENTION

The present invention contemplates methods, apparatuses, and systems for detecting and classifying airborne biological and non-biological particles, in real time, based on particle size, density, complex refractive index and auto-fluorescence content. According to the present invention, three physical phenomena are exploited in the detection scheme and involve the interaction of light with an aerosol particle: elastic scattering, absorption, and fluorescence. In addition to these optical phenomena, both a particle's size and density and complex refractive index are determined substantially simultaneously to enhance the particle's detection and identification/classification in real-time.

The present invention is directed to a method for detecting and classifying a single particle comprising illuminating the particle with a light beam having multiple excitation ranges. The particle has measurable and classifiable properties including size and density, complex refractive index, and auto-fluorescence content over different emission ranges. The size of a particle can be determined by measuring the elastic scatter intensity for a specific wavelength(s) and/or by its "time-of-flight" or the time a particle takes to traverse to light beams separated by a known distance upon exiting an accelerating orifice. Density of the particle can be determined by comparing a particle's elastic scatter intensity at one or more wavelengths with the particle's time-of flight. The auto-fluorescence content of the particle is measured by exciting the particle at specific wavelengths and detecting the fluorescence emission from endogenous fluorophores present in the particles of interest. Algorithms applied to classify a particle are based on the relationship of the above parameters to each other.

Further, the present invention is directed to a method for detecting and classifying a particle comprising providing and directing a sample stream containing particles to an optical viewing region and providing a plurality of continuous wave excitation sources, each source emitting a discrete wavelength. A plurality of discrete wavelengths of light from the continuous wave excitation sources is provided to the optical viewing region. Each particle found in the sample stream in the viewing region is illuminated with the excitation sources substantially simultaneously in real-time. Each particle has elastic scattering properties, fluorescence or non-fluorescence emission properties, and dimension and density properties. Light is directed from the viewing region to a plurality of detectors to produce a plurality of signals, and the signals are directed from the detectors to a signal processor to substantially simultaneously measure the elastic scattering properties, the complex refractive index and the fluorescence or non-fluorescence of the particle substantially simultaneously and in substantially real-time. In another preferred embodiment a continuous wave excitation source is used in tandem with a pulsed laser diode with nonlinear crystals to generate second and third harmonic wavelengths.

Still further, the present invention is directed to an apparatus for detecting and classifying a single particle from a sample comprising a plurality of continuous wave excitation sources, each source emitting a discrete wavelength, the wavelengths directed through an optical viewing region and a plurality of detectors to receive the wavelengths directed through the optical viewing region and produce a plurality of signals. A signal processor is in communication with each detector to receive the signal from the detector to substantially simultaneously measure the elastic scattering properties, the complex refractive index and the fluorescence or non-fluorescence of the particle substantially simultaneously and in substantially real time.

BRIEF DESCRIPTION OF THE DRAWINGS

FIG. 1a is a schematic representation illustrating a configuration of the present invention having a dual wavelength excitation with two elastic scatter detection channels and one fluorescence detection channel.

FIG. 1b is a schematic representation illustrating a configuration of the present invention having tri-wavelength excitation with three elastic scatter detection channels and two fluorescence detection channel.

FIG. 1c is a schematic representation illustrating a configuration of the present invention having a tri-wavelength excitation with three elastic scatter detection channels and one fluorescence detection channel.

FIG. 1d is a schematic representation illustrating a configuration of the present invention having a dual wavelength excitation with two elastic scatter detection channel.

FIG. 1e is a schematic representation illustrating a configuration of the present invention having a tri-wavelength excitation with three elastic scatter detection channels.

FIG. 1f is a schematic representation illustrating a configuration of the present invention having a single continuous wave excitation and two or three harmonically generated pulsed excitation wavelengths with one fluorescence detection channel and three to four elastic scatter detection channels.

FIGS. 2a–f are charted printouts of randomly sampled indoor aerosol particles.

FIGS. 3a–f are charted printouts of aerosol waveforms of BG Spores, 0.7 u PSL, and 1.0 u Fluorescent PSL.

FIG. 5a is a schematic representation of a single pulse trigger integrator mode of the present invention.

FIG. 5b is a schematic representation of a single pulse trigger integrator mode of the present invention, with pulse duration for long pulse rejection.

FIG. 5c is a schematic representation of a dual trigger pulse integration mode of the present invention, for laser drift correction.

FIG. 5d is a schematic representation of a dual trigger pulse integration mode of the present invention, with pulse duration for laser drift correction, and rejection of extra-long pulses.

FIG. 5e is a schematic representation of a dual trigger pulse integration mode of the present invention, with time-of-flight measurement measured by duration of aerosol travel between two excitation wavelengths and for extra-long pulse rejection.

DETAILED DESCRIPTION OF THE INVENTION

Figure 1A:
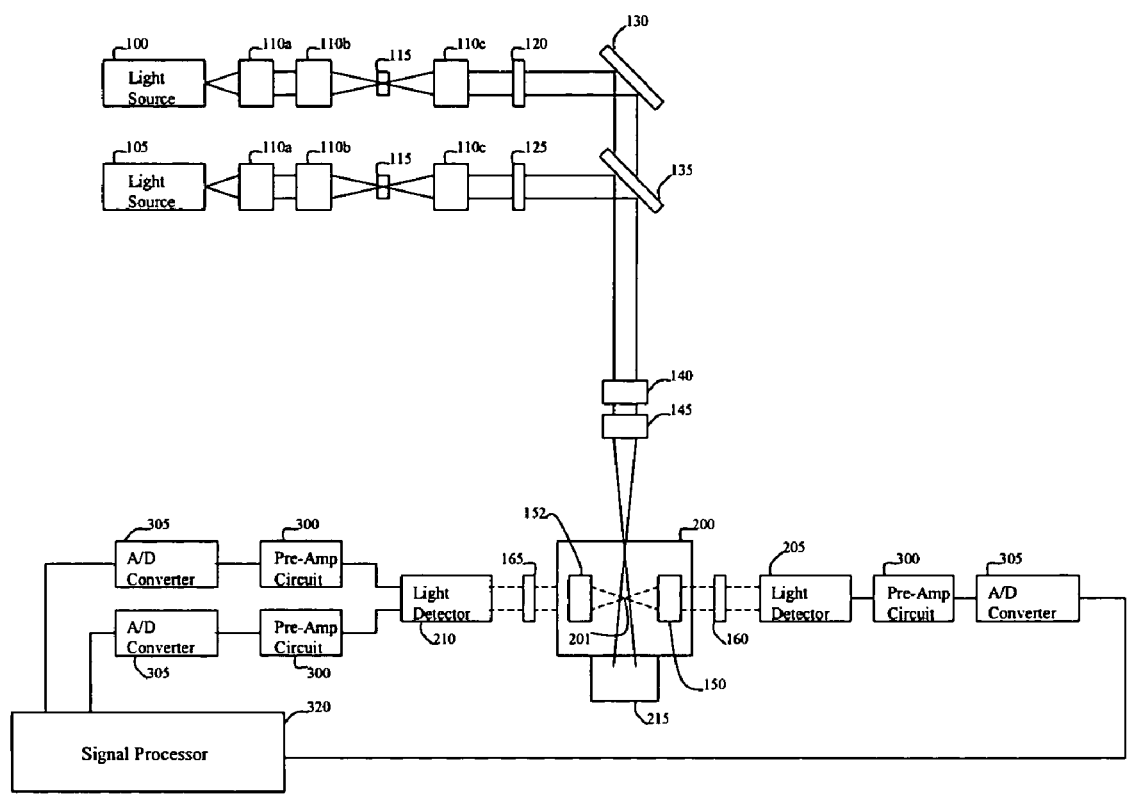
FIGS. 1a–1f illustrate aerosol sensing configuration block diagrams outlining various embodiments contemplated by the present invention.

The present invention relates to enhanced methods, apparatuses and systems for the detection and classification of biological and non-biological particulates in a real-time manner. There are three physical phenomena that are exploited in the detection scheme and involve the interaction of light with an aerosol particle: elastic scattering, absorption, and fluorescence. In addition to these optical phenomena, both a particle's size and density are determined substantially simultaneously. When considering scattering and absorption, the interaction of light with an aerosol particle is indicated by the complex refractive index of the particle material with respect to the medium in which the particle is suspended. The real and imaginary parts of the complex refractive index relate to the particle's refractive index and aerosol absorption index, respectively. This is defined as $m=n-ik$, where m is the complex refractive index, n is the refractive index and k is the aerosol absorption index. The complex refractive index is a function of the excitation wavelength and is dependent on the chemical composition of the particle. The real part of the complex refractive index provides information concerning the particle's size. A particle's absorptive properties can be measured indirectly by measuring the elastic scattering at two or more excitation wavelengths.

Model calculations of the influence of the complex refractive index on the scattering properties of a particle can be based on the Mie theory of light scattering assuming the particle is not too irregular in shape. The illumination method described herein involves excitation of individual aerosol particles excited one at a time. Using Mie theory, the sensor's response can be modeled and predicted. Discrete particulate counters measure the amount of light scattered into a given angular range from a single particle as it traverses a beam of light. The response R for a given scattering geometry is defined by this scattered light normalized to the excitation beam. For a linearly polarized light beam irradiating a particle from one direction the response is given by $$R = \frac{\lambda^2}{4\pi^2}\int_{\phi_1}^{\phi_2}\int_{\theta_1}^{\theta_2}(I_1(x,m,\theta,\phi)) + I_2(x,m,\theta,\phi))G(\theta,\phi)d\theta d\phi$$

where $I_1$ and $I_2$ are the scattered light intensities polarized parallel and perpendicular relative to the plane of oscillation of the electric vector of the incoming radiation, m is the complex refractive index and x is the dimensionless particle size parameter defined by $x=\pi D_p/\lambda$, with $D_p$ being the actual particle diameter and $\lambda$ the wavelength of the irradiation (1). $G(\phi,\theta)$ is a geometrical factor related to the specific optical design $\theta 1$ and $\theta 2$, together with $\phi_1$, and $\phi_2$, are truncation angles limiting the solid angle in which the scattered light is collected. By looking at this scattering response at two or more wavelengths information concerning the absorptive properties of a particle can be indirectly measured, as well as, its size. This technique can be used as a biological indicator through the appropriate selection of one or more excitation wavelengths that correspond to a peak absorption band for endogenous fluorophores or chromophores. Prediction of the degree of absorption by different types of aerosol particles can be achieved by looking at certain fluorophores or chromophores present in the particle using the following equation $$A = I_0 2.3\varepsilon C(2R)\left(1 + e^{-2}\int_1^0 e^{2x^2}dx\right)$$

where $I_0$ is the overall intensity of the laser beam, $\epsilon$ is the molar decadic absorption coefficient of the fluorophore or chromophore, C is the fluorophore/chromophore concentration in the particle, and R is the radius of the particle.

With this technique applied properly, a very sensitive response to the absorptive properties of the particle can be observed. The angular collection geometry and the excitation wavelengths used play a major role in the sensor's response. For example, one could observe an almost two orders of magnitude difference in the scattering intensity when comparing a 1 μm non-absorbing particle with a refractive index of 1.4 to a 1 μm absorbing particle with a refractive index of 1.4–0.5 i when excited at 630 nm and collecting backward scatter at 150° to 170°. If an angular collection geometry of 10° to 30° was employed, the intensity difference for the above particle types would be less than a factor of two.

The proper selection of the excitation wavelengths would also permit one to measure auto-florescence due to the presence of endogenous fluorophores within the biological particle. By employing two excitation wavelengths in the following ranges: 266–280 nm and 400–415 nm one can measure spectrally dispersed auto-fluorescence from, for example, the following endogenous fluorophores: aromatic amino acids, NADH, flavins, and chlorophylls.

According to one embodiment, the present invention contemplates the use of a third excitation wavelength that is a nonabsorbing or minimally absorbing wavelength for biological particles and falls into the visible to near-IR part of the electromagnetic spectrum, i.e. one that does not interfere with the fluorescence emission spectrum of the above fluorophores.

Using the three laser excitation approach of the present invention, with excitation in the following ranges 266–300 nm, 350–430 nm, and 600 nm–1.5 μm, one can measure the elastic scattering and absorptive properties of individual particles, as well as, the fluorescence emission of most of the endogenous fluorophores found in biological particles.

Therefore, according to the present invention, by dedicating three detection channels for the measuring the elastic scatter at each of the excitation wavelengths, and dedicating another three detection channels to the detection of the fluorescence emission of aromatic amino acids (300–400 nm), NADH and flavins (420–600 nm) and chlorophyll (600–700 nm) one is able to generate a seven dimensional or greater feature space (particle size, three elastic scattering channels, and three fluorescence channels) and a significantly enhanced classification scheme can be developed that is an improvement over all known detection methods.

According to the present invention, by providing separation of the one of the excitation beams from the other two, or separating all three from each other, the duration time for an individual aerosol particle can be measured as it is accelerated through each of the beams. Assuming a low Reynolds value (no turbulence), a particle's density can be determined from the time it takes the individual aerosol particle to traverse the beams. With the assumption that the velocities of a particle passing through two beams can be expressed as $v_1,=b_1,/\Delta t$, and $v_2=b_2-\Delta t_2$ the Stokes equation can be written in the following form:

$$m\frac{\Delta v}{\Delta t} = 6\pi\mu\alpha\frac{v_1 + v_2}{2}$$

where v is the velocity, $b_1$, and b2 are the widths of the beams, m is the mass of the particle (for spheres, m=4/$3R^3$p), $\Delta v=v_1-v_2$, $\Delta t$ is the time the particle takes to traverse two beams, μ is the viscosity of air and α is the radius of the a particle. From this equation, the density p can be calculated for spherical particles.

According to a further embodiment of the present invention, by determining a particle's density and size, as well as measuring the elastic scattering at three wavelengths and fluorescence at three wavelengths ranges, an eight dimensional or greater feature space can be created providing a further means for classifying biological and non-biological particles.

FIGS. 2 and 3 show oscilloscope traces of different types of individual particles showing two elastic scattering signals. The traces shown are excitation wavelengths of 405 nm and 785 nm. The differing amplitudes of the two signals for the various waveforms illustrate the influence the particle's absorptive properties has on the elastic scattering signal. FIG. 4 shows the theoretical response of a BG spore particle in comparison with an organic carbon particle for a two channel elastic scatter detection scheme. Two excitation wavelengths are represented (405 nm and 660 nm). The graph shows that for respirable range particulates by measuring the ratio of these two excitation wavelengths one is able to classify an organic carbon particle from a biological spore particle.

Described herein are seven aerosol sensing configurations which are variations of two or more excitation wavelengths and two or more detection channels. In all seven configurations aerosol is drawn into an optical viewing region at 0.5 to 30 liters per minute and particles are illuminated one at a time with two or more light beams. FIGS. 1*a*–1*g* provide block diagrams of the different configurations. In each of the configurations two or more of the following wavelength ranges are used for excitation: 266–300 nm, 350–430 nm, and 600–1500 nm. Three separate laser or LED sources can be used to provide excitation wavelengths in the above wavelength ranges or a single laser through the use of harmonic generation techniques. Additionally, one or more of the sources can operate in a modulated manner or as a continuous wave source. At least one of the excitation wavelengths is required to operate in a continuous manner to provide a triggering mechanism for the detection process. For the sources modulated, a modulation rate of 20 MHz or greater is preferred. Laser line generating optics are used to generate a laser line thickness of from about 5 to about 300μ, and a depth of field and laser line width that is at least two times (2×) the diameter of the inlet (aerosol orifice) employed. If three sources are employed to generate the three excitation wavelengths then the optics employed generate a laser line in one of three configurations: all three optically aligned and falling along the same axis orthogonal to the aerosol inlet probe, all three optically aligned with two falling along the same axis orthogonal to the aerosol inlet probe and the third separated at a defined distance from the other two along the same axis orthogonal to the aerosol inlet probe, and all three optically aligned with all three separated from each other at a defined distance along the same axis orthogonal to the aerosol inlet probe. Separation of the one or more of the laser lines from each other is for measurement of particle density and for particle sizing based on time of flight. Elastic scattering at each wavelength and fluorescence can be measured in any of the three laser line configurations mentioned above. If a single source is used with harmonic generation techniques, then all three excitation wavelengths are to be optically aligned and are to fall along the same axis orthogonal to the aerosol inlet probe. A laser line thickness of from about 5 to about 300μ provides a means for a short aerosol migration time permitting a high-count rate and a means for high optical energy density for optimal optical power illumination.

Various light collection geometries can be employed with different parameters applied for the different physical phenomena employed. For fluorescence, collection of fluorescence orthogonal to the direction of the light beam is recommended to minimize the effects of stray light on the fluorescence signal(s). For elastic scattering and absorbance collecting near forward scatter and back scatter separately, backscatter alone, side angle scatter alone, and side scatter and back scatter together are optimal collection geometries for separating the scattering component of an aerosol from the absorptive component.

FIG. 1*a* illustrates a configuration whereby two excitation sources are employed and three detection channels: two for elastic scatter at two different wavelengths and one for fluorescence detection. Aerosol is drawn into the sensor cell 200 through an aerosol nozzle (not shown) and is introduced into an optical viewing region 201. Two excitation sources 100, 105 are employed. The excitation sources 100, 105 can be either a continuous source or modulated at 20 MHz or greater frequency and can be a laser, light emitting diode or some other light emitting device. Excitation source 100 is a longer wavelength than excitation source 105 in one of the two wavelength ranges 350–430 nm and 600–1500 nm. Excitation source 105 is a shorter wavelength than excitation source 100 and emits in one of two wavelength ranges: 266–300 nm or 350–430 nm. Light emitted from these sources are collimated using an aspheric lens 110*a* and then spatially filtered by focusing the collimated light using another aspheric lens 110*b* onto a pin hole aperture 115 and then re-collimated using another aspheric lens 110*c*. Collimated light from both sources can then be introduced to a narrow bandpass filters 120, 125 for removal of unwanted wavelengths emitted from sources 100 and 105 or from auto-fluorescence produced from the optical elements. Collimated light from both excitation sources 100, 105 are introduced to dichroic mirrors 130 and 135 positioned at 45 degrees relative to the collimated light. Dichroic mirrors 130 and 135 provide the means for alignment of the two collimated sources onto the same optical train and also provide the primary means for optical alignment. The two collimated beams can be aligned to fall along the same path or can be separated along the plane orthogonal to the aerosol inlet nozzle so that particle time-of-flight and density measurements can be performed. Dichroic mirrors 130 and 135 also provide additional optical filtering by removing unwanted wavelengths emitted from sources 100 and 105 or from auto-fluorescence of the optical elements. Light exiting dichroic mirrors 130 and 135 is then introduced to a series a beam shaping optics creating a sheet of light at the aerosol nozzle region that is from about 5 to about 300 μ in thickness and a depth of field and beam width that is at least two times (2×) larger than the diameter of the inlet (e.g. aerosol nozzle). In one embodiment, a spherical lens 140 and a cylindrical lens 145 are used to generate the above geometry. In one preferred embodiment of the present invention, a spherical lens 140 and a Powell lens 145 are used.

The two light beams generated from the beam shaping elements 140 and 145 are then introduced into the optical viewing region 201. Particles are illuminated, one at a time, in this region 201 with an aerosol migration time of 100 to 2000 nanoseconds. Light exiting this region in the forward direction is collected using a light trap 215.

In the embodiment illustrated in FIG. 1*a*, light both emitted as elastic scatter and as fluorescence is side angle collected over the range of from about 65 to about 115 degrees using light collection lenses 150, 152. The light collection lenses 150, 152 collect light emitted in the illumination region over the range of from about 65 to about 115 degrees and then collimate the light for introduction to bandpass filters 160 and 165 and finally to the light receiving elements (light detectors) 205 and 210. The collector lenses 150, 152 can be aspheric condensers, cylindrical lenses, or diffractive optical elements.

Two collector lenses 150, 152 are used in this embodiment. One is used for collecting elastically scattered light emitted by the particle from both of the excitation wavelengths and one is used for collecting fluorescence emission from the illuminated particle. Elastically scattered light at the two excitation wavelengths is then introduced to a narrow bandpass filter element 165. The filter element 165 is comprised of two halves with one region filtering all wavelengths but that desired from source 100 and the other region filtering all wavelengths but that desired from source 105. For the fluorescence channel, filter element 160 is used to filter out all wavelengths except a wavelength range that corresponds to a fluorescence emission for a certain fluorophore or group of fluorophores commonly encountered in a biological or non-biological particle.

Elastically scattered light that has been filtered using filter element 165 is then introduced to a light receiving element (light detector) 210. The light receiving element is a detector array having two or more detector elements such as a photomultiplier tube array, silicon photodiode array or avalanche photodiode array. Fluorescence emission that has been filtered using filter element 160 is introduced to a single receiving element (light detector) 205 such as a photomultiplier tube, avalanche photodiode, or a silicon photodiode that has a similar sensitivity as a photomultiplier tube or avalanche photodiode. Signals from both light receiving elements 205 and 210 are then introduced to a preamplifier circuits 300 whereby a 100–2000 nanosecond current pulse is converted first to an analog voltage and then to a digital signal using an analog-to-digital converter 305. The signals from all three channels are then introduced to a signal processor 320 for analysis. The signal processor 320 can be a microcontroller, digital signal processor, field programmable gate array or a microcomputer, as would be readily understood by one skilled in the field of signal processing.

The preamp circuits 300 can be configured to serve analog signal processing functions. For each of the aerosol sensor configurations illustrated in FIGS. 1a–1g, the pre-amp circuit can be configured to provide the following functions: an analog input bandwidth sufficient to capture 100 nanosecond current pulses, triggering of pulse detector from analog voltage level from one or two of the elastic scatter detection channels, suppression of noise from very short (approximately 20 nanoseconds) non-aerosol pulses present at the light detector outputs, integration and holding of light detector pulses over the duration of the trigger pulse (roughly 100–2000 nanoseconds), production of a pulse output level proportional to the pulse width, and the production of an analog to digital conversion trigger signal after the current pulse generated from an aerosol event is finished.

FIGS. 5a–5h illustrate some of the contemplated analog signal processing configurations. Using these approaches aerosol events are triggered by monitoring one or two elastic scatter channels followed by the integration and/or peak detection of the analog signal generated from the elastic scatter channels, integrating the signals generated from the fluorescent detection channels during the trigger period, measuring the pulse duration during the trigger period, and measuring of the time-of-flight period between two elastic scatter channels if two of the light beams are purposely separated from each other by a known distance.

Figure 5A:
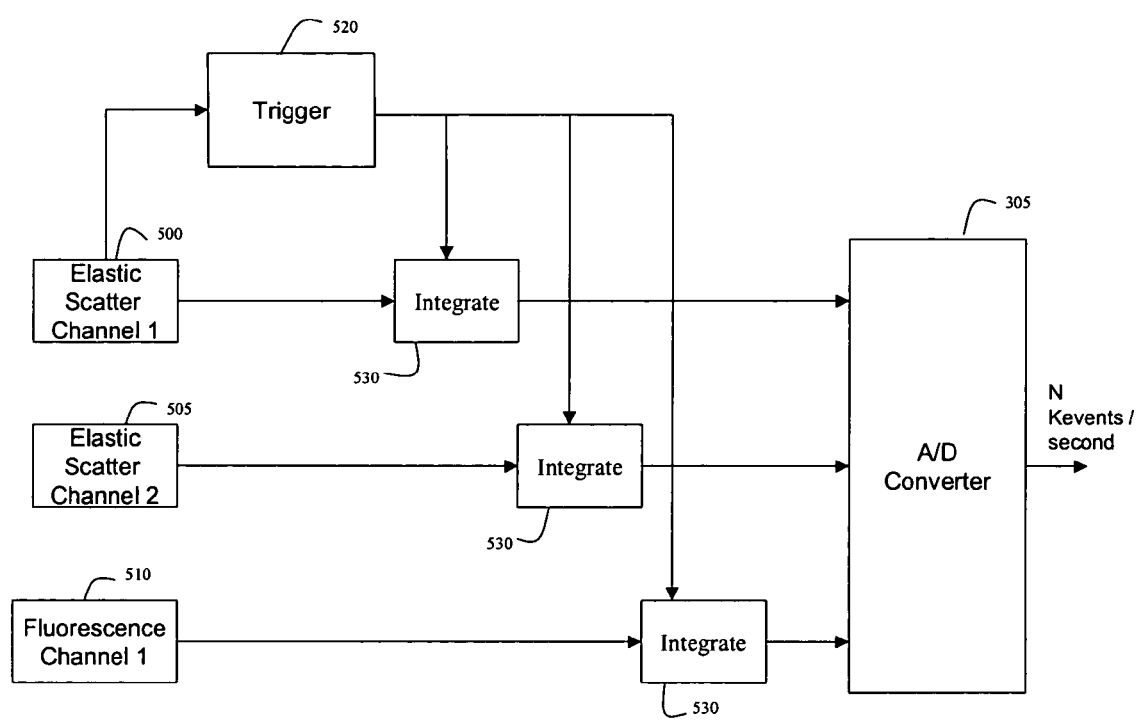
FIGS. 5a–e illustrate analog signal processing configurations for dual excitation wavelength aerosol sensing.

More specifically, FIG. 5a is a schematic diagram illustrating an analog signal processing configuration for a dual wavelength excitation scheme as illustrated in FIG. 1a. FIG. 5a illustrates a single pulse trigger signal integration approach contemplated by the present invention. Elastic scatter channel 1 500 is used to trigger the presence of an aerosol event. The trigger 520 monitors the voltage level of elastic scatter channel 1 500 and triggers signal integration 530 for each of the two elastic scatter detection channels 500 and 505, as well as, fluorescence channel 1 510. The integrator 530 integrates the signal for each of the detection channels over the duration of the trigger pulse and holds the voltage generated for each until inputted into the analog to digital converter 305. The analog to digital converter 305 then converts the voltage into a digital signal for analysis by the signal processor 320. (See FIGS. 1a–1h).

Figure 5B:
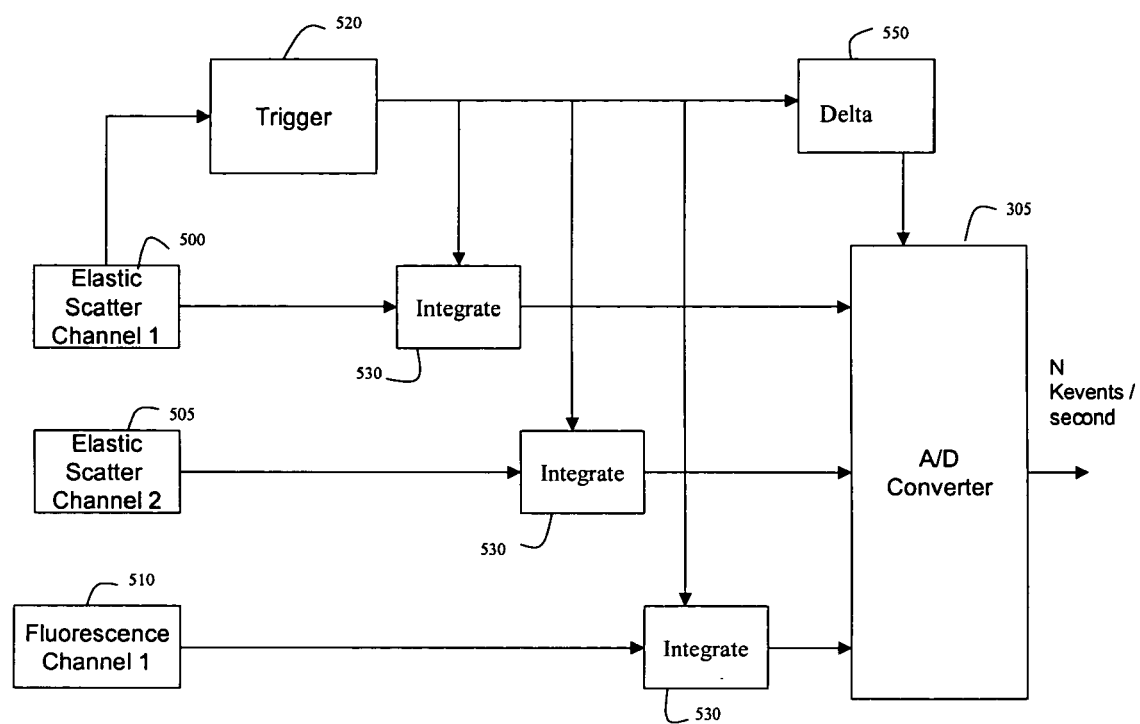

FIG. 5b is a schematic diagram that illustrates another analog signal processing configuration for a dual wavelength excitation scheme as illustrated in FIG. 1a. FIG. 5a illustrates a single pulse trigger signal integration approach with an additional means for measuring pulse duration for rejecting aerosol events that exceed a certain time period. This permits the exclusion of aerosol events that occur within the sensor cell 200 due to the re-circulation of particles at lower velocities after particles have exited the optical illumination region 201 the first time. (See FIGS. 1a–1h). In this approach, as shown in FIG. 5b, in addition to the signal integration of channels 500, 505, and 510, the time period or delta 550 that the trigger is on for elastic scatter channel 1 500 is measured by producing an output voltage that is proportional to the pulse width. This voltage is also converted by the analog to digital converter 305 for analysis by the signal processor 320. (See FIGS. 1a–1h).

Figure 5C:
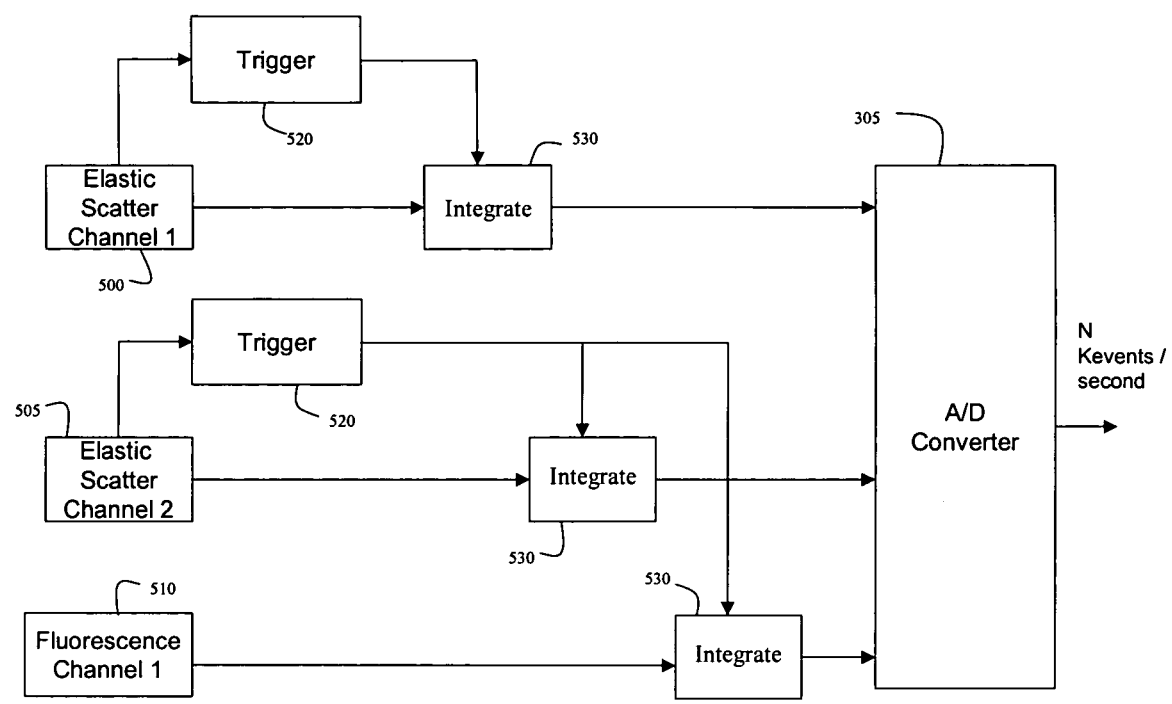

FIG. 5c is a schematic diagram that illustrates another analog signal processing configuration, contemplated by the present invention, for a dual wavelength excitation scheme as illustrated in FIG. 1a. FIG. 5c illustrates a dual trigger 520, 522 pulse integration approach that provides an additional means for laser drift correction. In this approach both elastic scatter channels 1 and 2, 500, 505 are used to trigger the integration of the detection channels. Drifting of one of the excitation beams from the other can be compensated for using this approach.

Figure 5D:
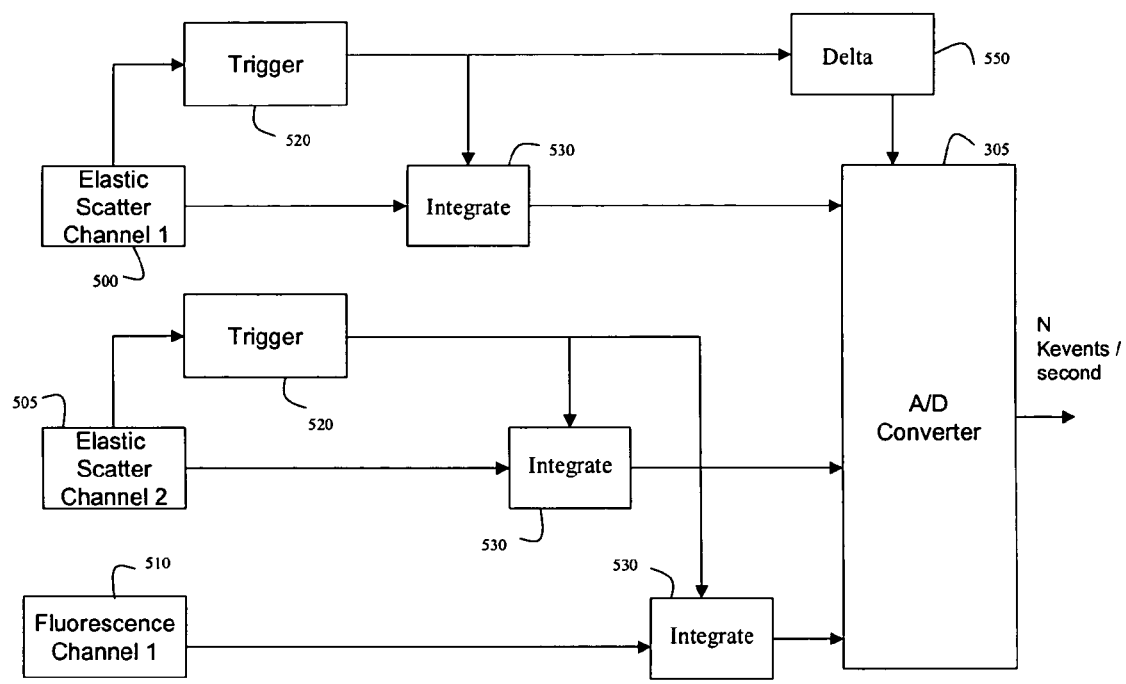

FIG. 5d is a schematic diagram that illustrates another analog signal processing configuration as contemplated by the present invention, for a dual wavelength excitation scheme as illustrated in FIG. 1a. This approach is similar to the approach illustrated in FIG. 5c with the addition of the measurement of the pulse duration for elastic scatter channel 1 as described above.

Figure 5E:
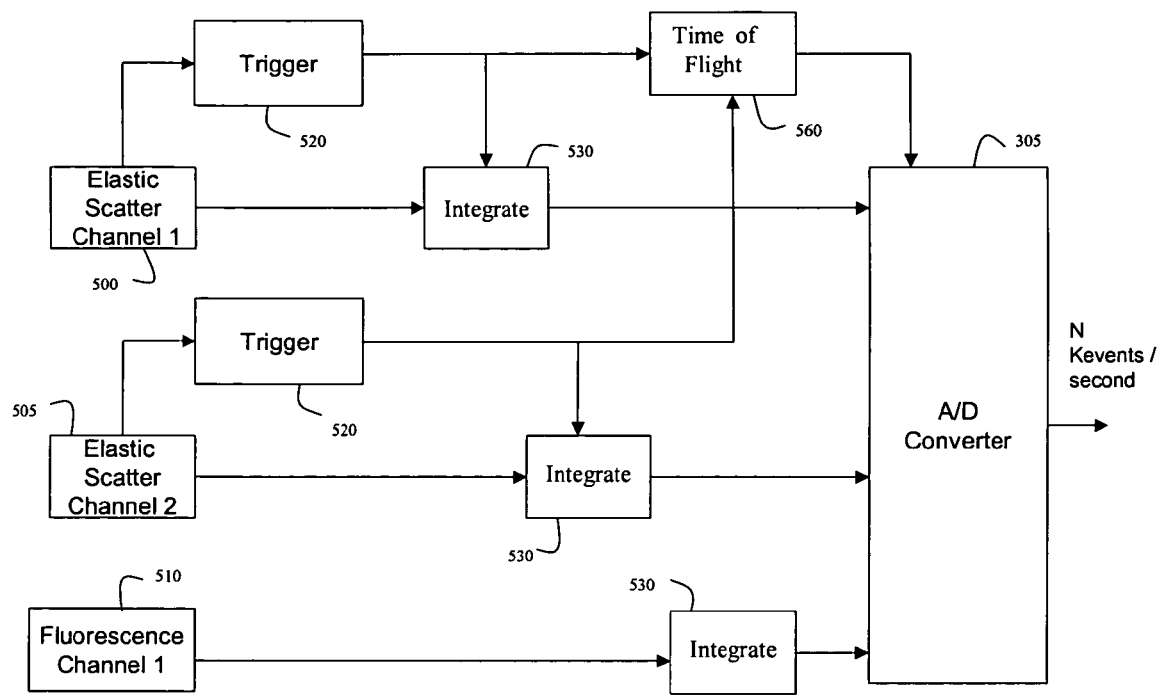

FIG. 5e is a schematic diagram that illustrates another analog signal processing configuration contemplated by the present invention for a dual wavelength excitation scheme as illustrated in FIG. 1a. For this approach the two excitation beams are separated by a known distance orthogonal to the aerosol inlet nozzle (not shown) and through the use of a dual trigger 520, 522 on elastic scatter channels 1 and 2, 500, 505 a particle's time period for traversing the two beams or "time-of-flight" can be measured. This approach still permits the integration of all three detection channels, laser drift correction, and long pulse rejection.

Figure 1B:
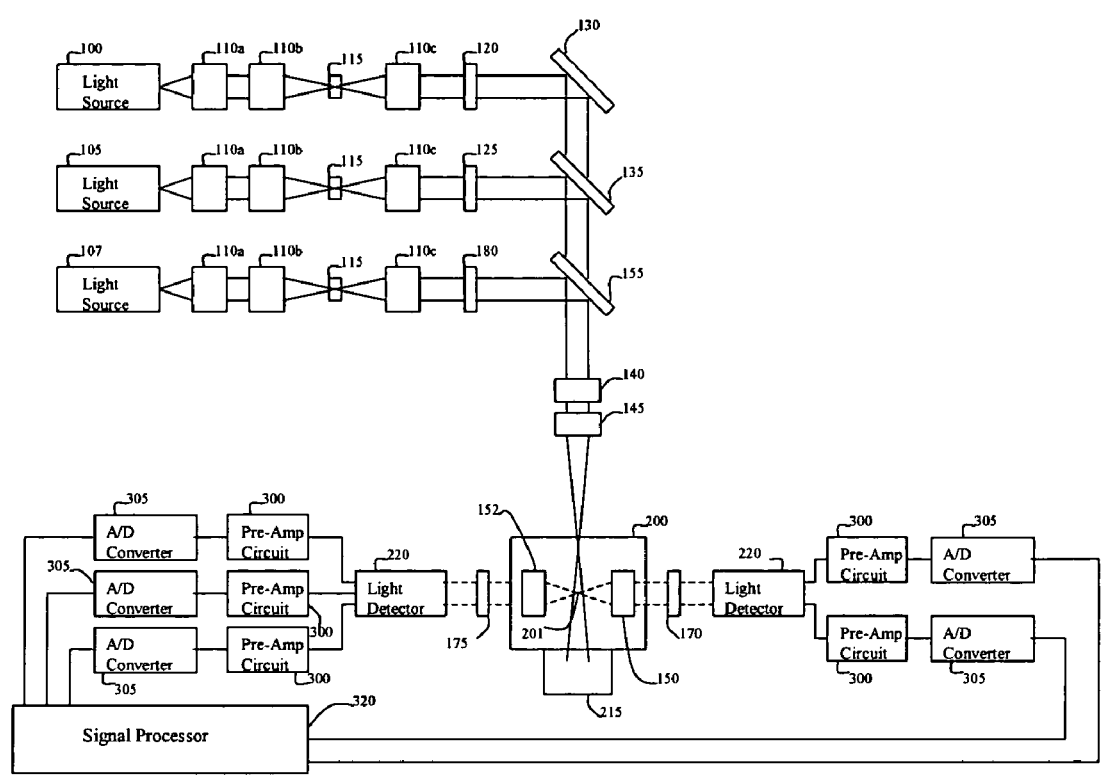

For purposes of illustration FIGS. 1b–1h provide variations of that described for FIG. 1a. FIG. 1b is a schematic diagram that illustrates three excitation sources with three elastic scatter detection channels and two fluorescence detection channels. The excitation sources 100, 105, 107 can be either a continuous source or modulated at 20 MHz or greater frequency and can be a laser, light emitting diode or some other light emitting device. For purposes of the present application, the terms "continuous wave source" or "continuous source" are understood to encompass both continuous wave light emitting devices and such devices modulated at 20 MHz or greater. These devices are understood to be lasers, light emitting diodes (LEDs) or other light emitting devices. Excitation source 100 is a longer wavelength than excitation source 105, 107 in the wavelength range of 600–1500 nm. Excitation source 105 is a shorter wavelength than excitation source 100 and emits in the range of 350–430 nm. Excitation source 107 is a shorter wavelength than excitation source 100, 105 and emits in the range of 266–300 nm. Narrow bandpass filters 120,125,180 are used for removal of unwanted wavelengths emitted from sources 100,105,107 or from auto-fluorescence produced from the optical elements. The same beam shaping optics approach as illustrated in FIG. 1a is applied. The three collimated beams can be aligned to fall along the same path or one of the three can be separated from the other two along the plane orthogonal to the aerosol inlet nozzle so that particle time-of-flight and density measurements can be performed. Two light receiving elements 220 are used for receiving light generated by the particle. The light receiving element is a detector array having two or more detector elements such as a photomultiplier tube array, silicon photodiode array or avalanche photodiode array. For two channel fluorescence detection filter element 170 is used and is comprised of two halves with one region filtering all wavelengths but that of the desired fluorescence emission range of 430–580 nm for excitation source 105 and the other region filtering all wavelengths but that of the desired fluorescence emission range of 290–390 nm for excitation source 107. For three channel elastic scatter detection filter element 175 is used and is comprised of three narrow bandpass filter sections of the same type as used in the narrow bandpass filters 120, 125,180.

Figure 1C:
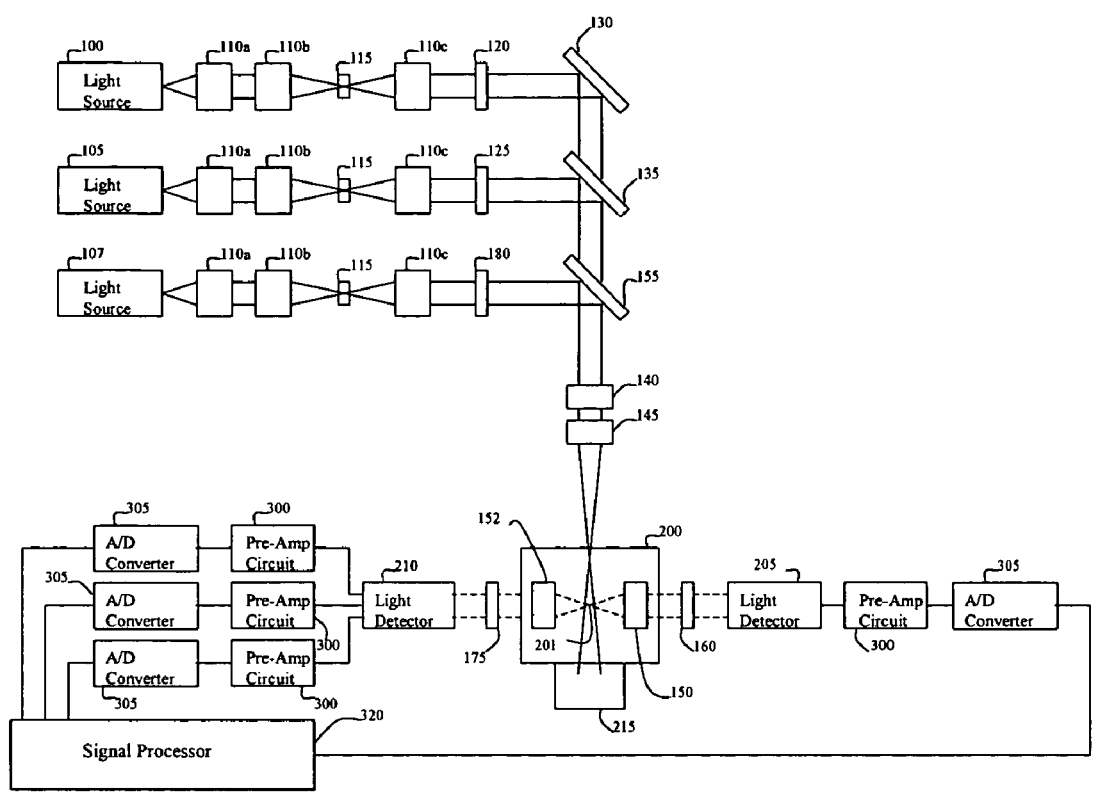

FIG. 1c is a schematic diagram that illustrates three excitation sources with three elastic scatter detection channels and one fluorescence detection channel. The excitation sources 100, 105, 107 can be either a continuous source or modulated at 20 MHz or greater frequency and can be a laser, light emitting diode or some other light emitting device. Excitation source 100 is a longer wavelength than excitation source 105, 107 in the wavelength range of 600–1500 nm. Excitation source 105 is a shorter wavelength than excitation source 100 and emits in the range of 350–430 nm. Excitation source 107 is a shorter wavelength than excitation source 100, 105 and emits in the range of 266–300 nm. Narrow bandpass filters 120,125,180 are used for removal of unwanted wavelengths emitted from sources 100,105,107 or from auto-fluorescence produced from the optical elements. The same beam shaping optics approach as illustrated in FIG. 1a is applied. The three collimated beams can be aligned to fall along the same path or one of the three can be separated from the other two along the plane orthogonal to the aerosol inlet nozzle so that particle time-of-flight and density measurements can be performed. For Elastic scatter detection receiving element 220 is used for receiving light generated by the particle. The light receiving element is a detector array having two or more detector elements such as a photomultiplier tube array, silicon photodiode array or avalanche photodiode array. For one channel fluorescence detection the fluorescence emission from the particle is filtered using filter element 160 which filters all wavelengths but that of the desired fluorescence emission range of 430–580 nm or 290–390 nm. Filtered light is then introduced to a single receiving element (light detector) 205 such as a photomultiplier tube, avalanche photodiode, or a silicon photodiode that has a similar sensitivity as a photomultiplier tube or avalanche photodiode. For three channel elastic scatter detection filter element 175 is used and is comprised of three narrow bandpass filter sections of the same type as used in the narrow bandpass filters 120,125, 180.

Figure 1D:
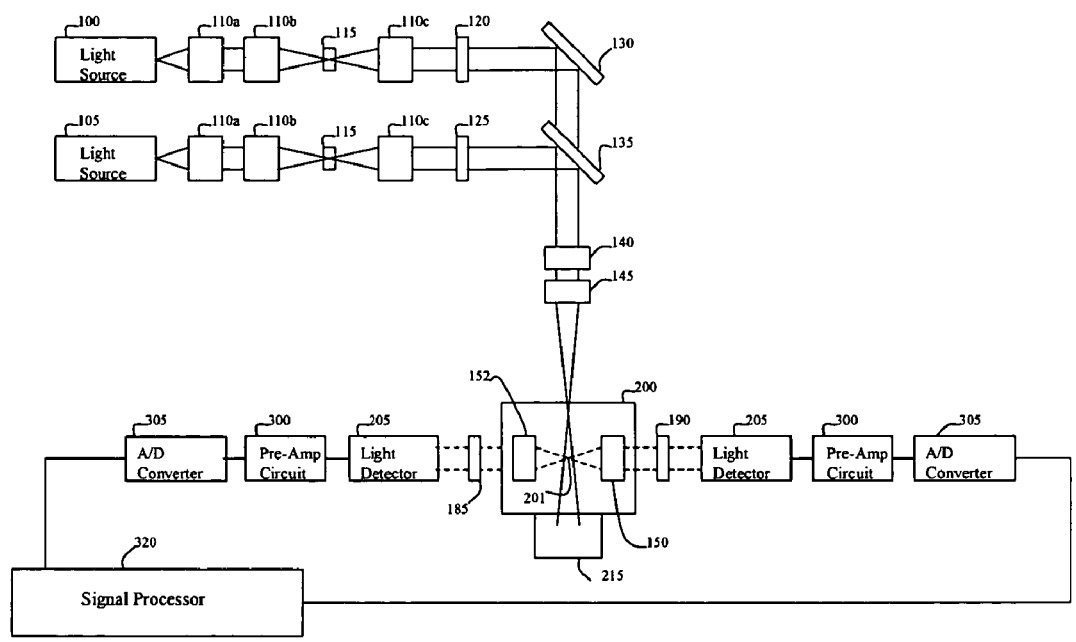

FIG. 1d is a schematic diagram that illustrates two excitation sources with two elastic scatter detection channels and no fluorescence detection channel. The excitation sources 100, 105, can be either a continuous source or modulated at 20 MHz or greater frequency and can be a laser, light emitting diode or some other light emitting device. Excitation source 100 is a longer wavelength than excitation source 105 in the wavelength range of 600–1500 nm. Excitation source 105 is a shorter wavelength than excitation source 100 and emits either in the range of of 266–300 nm or 350–430 nm. Narrow bandpass filters 120, 125 are used for removal of unwanted wavelengths emitted from sources 100, 105 or from auto-fluorescence produced from the optical elements. The same beam shaping optics approach as illustrated in FIG. 1a is applied. The two collimated beams can be aligned to fall along the same path or can be separated along the plane orthogonal to the aerosol inlet nozzle so that particle time-of-flight and density measurements can be performed. For elastic scatter detection narrow bandpass filter elements 185,190 are used of the same type as filters 120, 125, respectively. Filtered light is then introduced to a single receiving element (light detector) 205 such as a photomultiplier tube, avalanche photodiode, or a silicon photodiode.

Figure 1E:
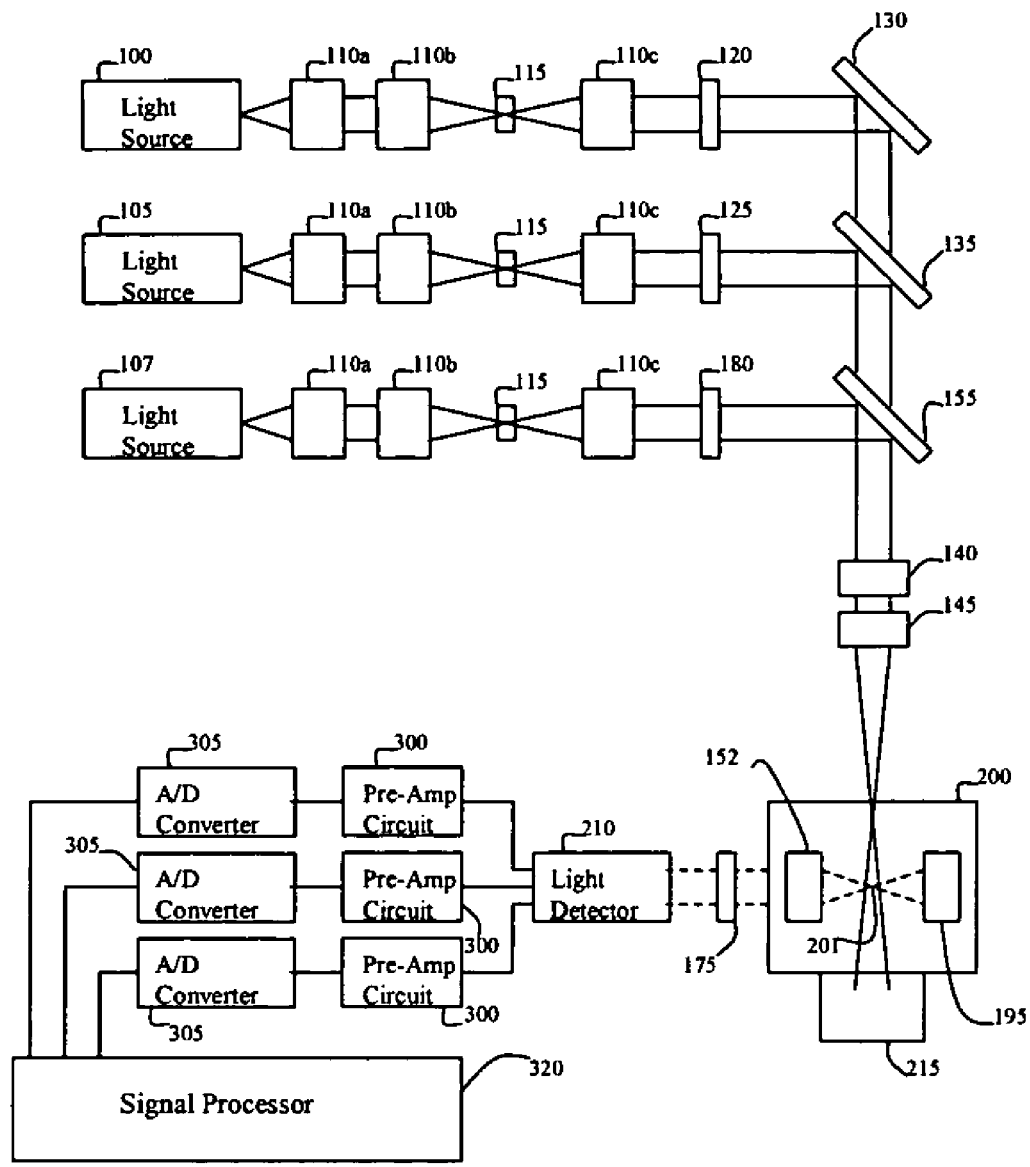

FIG. 1e is a schematic diagram that illustrates three excitation sources with three elastic scatter detection channels and no fluorescence detection channels. The excitation sources 100, 105, 107 can be either a continuous source or modulated at 20 MHz or greater frequency and can be a laser, light emitting diode or some other light emitting device. Excitation source 100 is a longer wavelength than excitation source 105, 107 in the wavelength range of 600–1500 nm. Excitation source 105 is a shorter wavelength than excitation source 100 and emits in the range of 350–430 nm. Excitation source 107 is a shorter wavelength than excitation source 100, 105 and emits in the range of 266–300 nm. Narrow bandpass filters 120,125,180 are used for removal of unwanted wavelengths emitted from sources 100,105,107 or from auto-fluorescence produced from the optical elements. The same beam shaping optics approach as illustrated in FIG. 1a is applied. The three collimated beams can be aligned to fall along the same path or one of the three can be separated from the other two along the plane orthogonal to the aerosol inlet nozzle so that particle time-of-flight and density measurements can be performed. For Elastic scatter detection receiving element 210 is used for receiving light generated by the particle. The light receiving element is a detector array having three or more detector elements such as a photomultiplier tube array, silicon photodiode array or avalanche photodiode array. A reflector element 195 is used on one side of sensor cell 200 to reflect light scattered from a particle onto light detector 210. One example of a reflector element 195 is an aspheric condenser lens and mirror combination which collects side scattered light, collimates it onto the surface of the mirror then refocuses the light back into the optical viewing region followed by collection by lens 152.

Figure 1F:
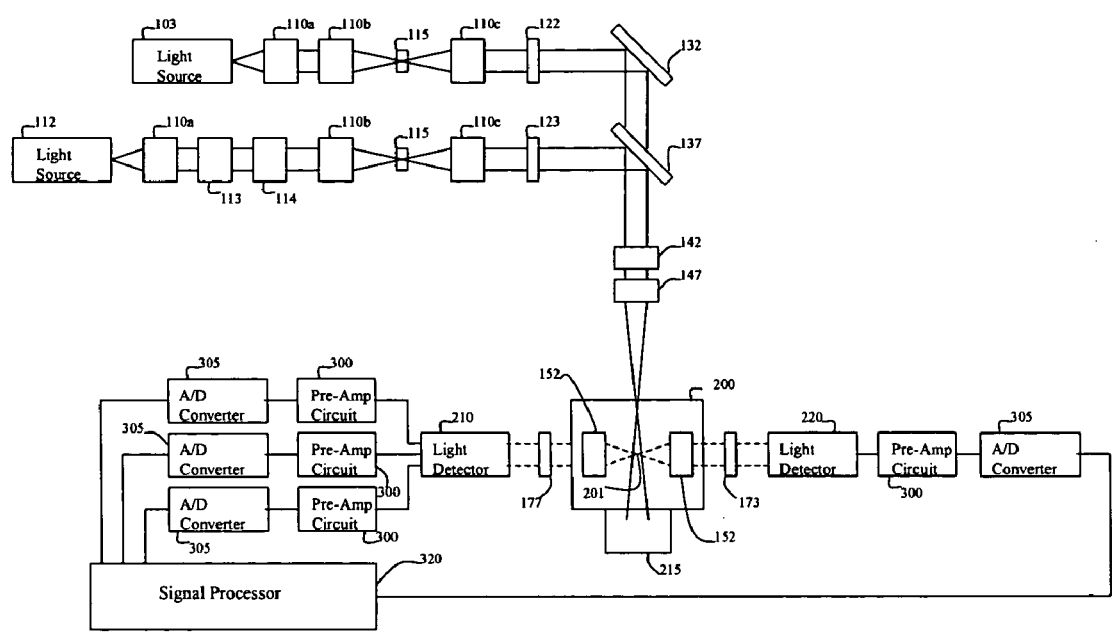

FIG. 1f is a schematic diagram that illustrates two excitation sources with three to four elastic scatter detection channels and one fluorescence detection channel. Excitation source 103 can be either a continuous source or modulated at 20 MHz or greater frequency and can be a laser, light emitting diode or some other light emitting device. Excitation source 112 is a pulsed laser diode. Nonlinear crystals 113, 114 are used to generate second and third harmonic frequencies. In this approach excitation source 112 is fired when the system detects the presence of a particle. Excitation source 103 is required to have a wavelength equal to or longer than excitation source 112 and narrow bandpass filter 122 filters any unwanted wavelengths. One example is to use a 1500 nm laser diode for excitation source 103 and a 1064 nm laser diode for excitation source 112. Second and third harmonic generation of a 1064 nm source would produce harmonics at 532 nm and 266 nm, respectively. The same beam shaping optics approach as illustrated in FIG. 1a is applied. For Elastic scatter detection receiving element 210 is used for receiving light generated by the particle. The light receiving element is a detector array having three or more detector elements such as a photomultiplier tube array, silicon photodiode array or avalanche photodiode array. For one channel fluorescence detection the fluorescence emission from the particle is filtered using filter element 160 which filters all wavelengths but that of the desired fluorescence emission range of 430–580 nm or 290–390 nm. Filtered light is then introduced to a single receiving element (light detector) 205 such as a photomultiplier tube, avalanche photodiode, or a silicon photodiode that has a similar sensitivity as a photomultiplier tube or avalanche photodiode. For three to four channel elastic scatter detection filter element 177 is used and is comprised of three to four narrow bandpass filter sections specific for the three excitation wavelengths provided by excitation source 112 and crystals 113, 114 and from excitation source 103.

Figure 1G:
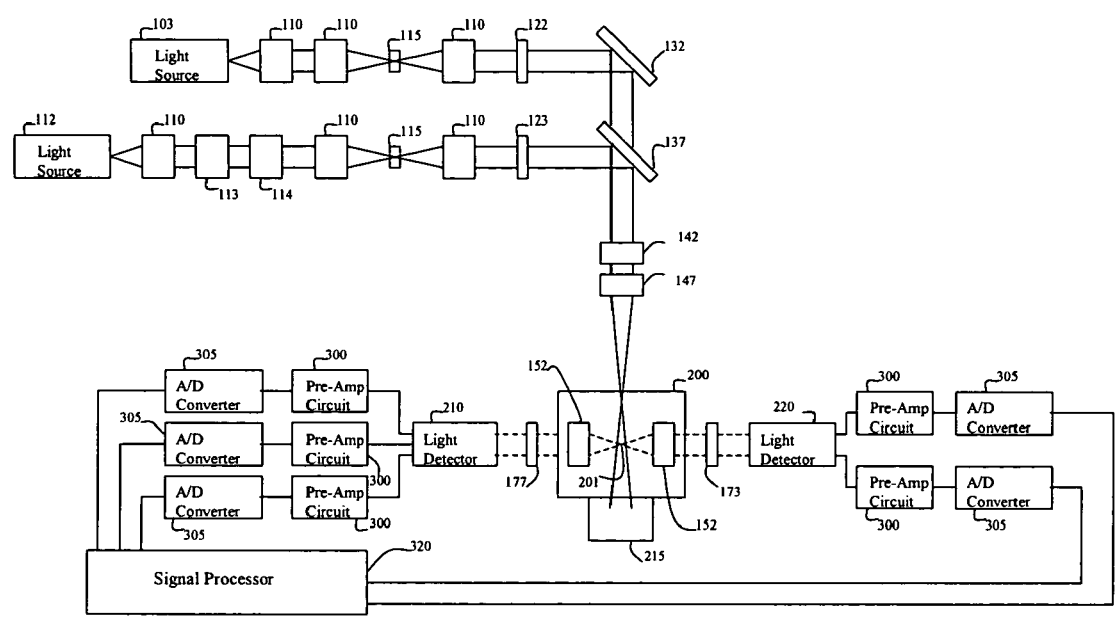
FIG. 1g is a schematic representation illustrating a configuration of the present invention having a single continuous wave excitation and two or three harmonically generated pulsed excitation wavelengths with two fluorescence detection channels and three to four elastic scatter detection channels.
Figure 1H:
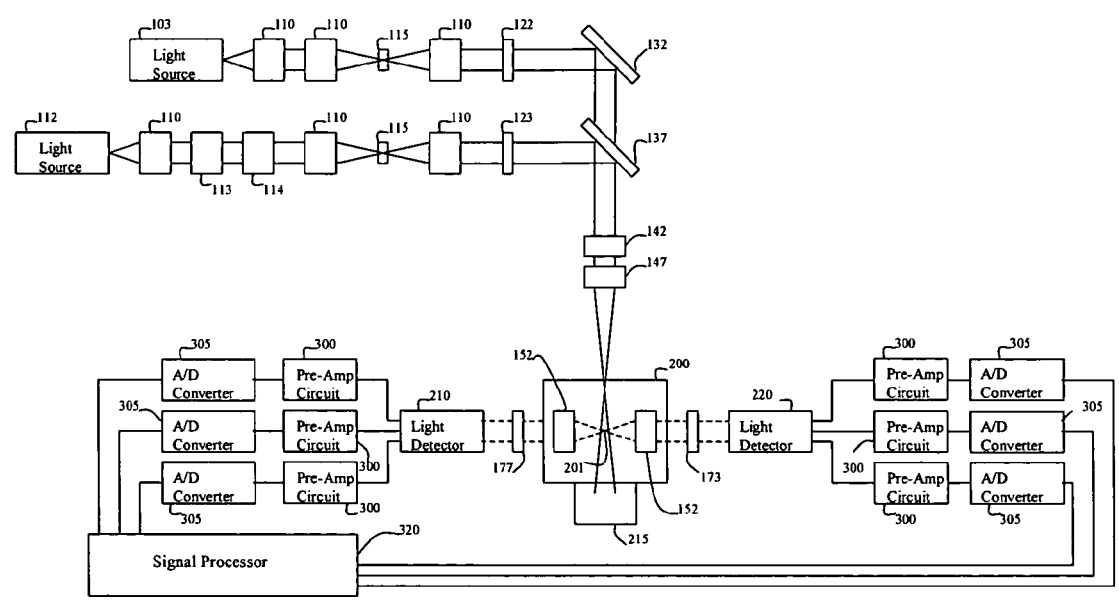
FIG. 1h is a schematic representation illustrating a configuration of the present invention having a single continuous wave excitation and two or three harmonically generated pulsed excitation wavelengths with three fluorescence detection channels and three to four elastic scatter detection channels.
Figure 4:
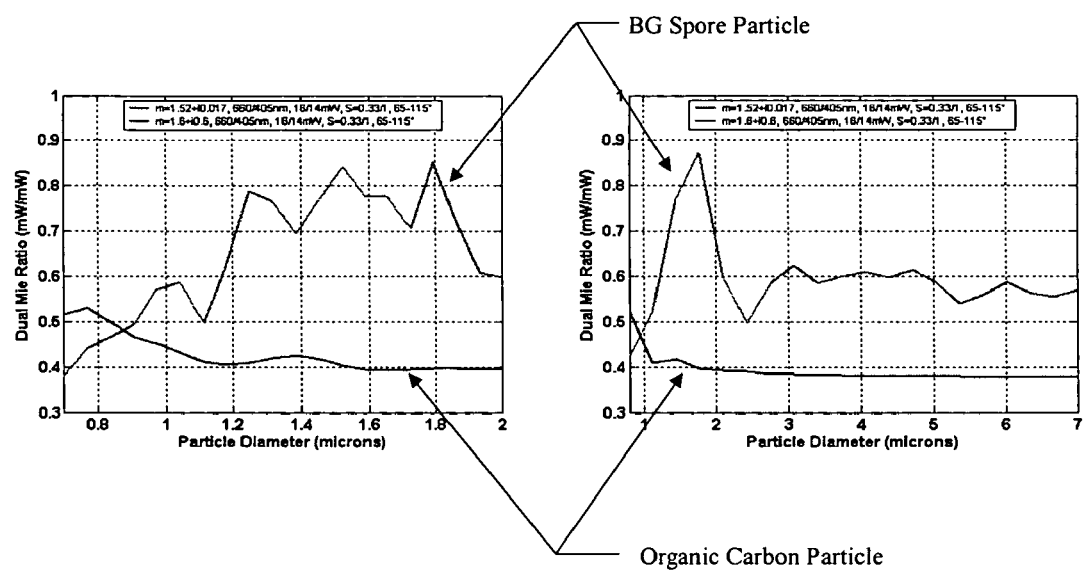
FIG. 4 are plotted graphs showing a theoretical response for BG Spore vs. Organic Carbon Particle.

FIG. 1g is a schematic diagram that illustrates two excitation sources with three to four elastic scatter detection channels and two fluorescence detection channels. Excitation source 103 can be either a continuous source or modulated at 20 MHz or greater frequency and can be a laser, light emitting diode or some other light emitting device. Excitation source 112 is a pulsed laser diode. Nonlinear crystals 113, 114 are used to generate second and third harmonic frequencies. In this approach excitation source 112 is fired when the system detects the presence of a particle. Excitation source 103 is required to have a wavelength equal to or longer than excitation source 112 and narrow bandpass filter 122 filters any unwanted wavelengths. One example is to use a 1500 nm laser diode for excitation source 103 and a 1064 nm laser diode for excitation source 112. Second and third harmonic generation of a 1064 nm source would produce harmonics at 532 nm and 266 nm, respectively. The same beam shaping optics approach as illustrated in FIG. 1a is applied. Two light receiving elements 220 are used for receiving light generated by the particle. The light receiving element is a detector array having two or more detector elements such as a photomultiplier tube array, silicon photodiode array or avalanche photodiode array. For two channel fluorescence detection filter element 174 is used and is comprised of two halves with one region filtering all wavelengths but that of the desired fluorescence emission range of 430–580 nm and the other region filtering all wavelengths but that of the desired fluorescence emission range of 290–390 nm. For three to four channel elastic scatter detection filter element 177 is used and is comprised of three to four narrow bandpass filter sections specific for the three excitation wavelengths provided by excitation source 112 and crystals 113, 114 and from excitation source 103.

It is contemplated that the present particle detection and classification invention is highly useful when incorporated into various environments requiring immediate particle detection and classification. Such environments include the indoor and out-of-doors environments. Therefore, the present invention may be incorporated into any open environment, or any closed environment such as buildings, vehicles, or any other enclosed structure. It is understood that "vehicles" include both manned and unmanned enclosed spaced or objects including cars, truck, tanks, boats, airplanes, space stations including all military and non-military type applications.

EXAMPLES

The following Examples summarize the preferred sensor configurations of the present invention. Note that for each Example, both time-of-flight and particle density can be measured substantially simultaneously with the appropriate/same detection channels Example 1

System Variation 1:
　Two continuous wave excitation sources (laser diode or LED)
　Source 1 (600–1500 nm)
　Source 2 (266–300 nm or 350–430 nm)
　Detection Channels: two elastic scatter (narrow band within 600–1500 & 266–300 or 350–430)
　one fluorescence
　ex266–300 emission 310–580
　ex350–430 emission 430–580

Example 2

System Variation 2
　Three continuous waves excitation sources (laser diode or LED)
　Source 1 (600–1500 nm)
　Source 2 (400–430 nm)
　Source 3 (266–300 nm)
　Detection Channels: three elastic scatter (narrow band within above three)
　Two fluorescence
　Ex266–300 emission 310–390
　Ex400–430 emission 430–580

Example 3

System Variation 3
　Three continuous waves excitation sources (laser diode or LED)
　Source 1 (600–1500 nm)
　Source 2 (400–430 nm)
　Source 3 (266–300 nm)
　Detection Channels: three elastic scatter (narrow band within above three)
　One fluorescence
　Ex266–300 emission 310–390
　Ex400–430 emission 430–580

Example 4

System Variation 4
　Two continuous wave excitation sources (laser diode or LED)
　Source 1 (600–1500 nm)
　Source 2 (266–300 nm or 350–430 nm)
　Detection Channels: two elastic scatter only (narrow band within 600–1500 & 266–300 or 350–430)

Example 5

System Variation 5
　Three continuous waves excitation sources (laser diode or LED)
　Source 1 (600–1500 nm)
　Source 2 (400–430 nm)
　Source 3 (266–300 nm)
　Detection Channels: three elastic scatter only (narrow band within above three)

Example 6

System Variation 6
　Single continuous wave laser diode (1500 nm) or LED as trigger and pulsed laser diode with nonlinear crystals for second and third harmonic wavelength generation
　Detection Channels: three elastic scatter (narrow bands from pulsed source)
　1064, 532, 266
　one fluorescence
　Ex266 emission 290–580

Example 7

System Version 7
  Single continuous wave laser diode (1500 nm) or LED as trigger and pulsed laser diode with nonlinear crystals for second and third harmonic wavelength generation
  Detection Channels: three elastic scatter (narrow bands from pulsed source)
  1064, 532, 266
  two fluorescence
  Ex266 emission 290–380
  Ex400–430 emission 430–580

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of steps set forth in the specification should not be construed as limitations on the claims. In addition, the claims directed to the method and/or process of the present invention should not be limited to the performance of their steps in the order presented, and one skilled in the art can readily appreciate that the sequences may be varied and still remain within the spirit and scope of the present invention.

We claim:

1. A method for detecting and classifying a particle comprising the steps of:
  providing and directing a sample stream containing particles to an optical viewing region;
  providing a plurality of continuous wave excitation sources, each source emitting a discrete wavelength;
  directing a plurality of discrete wavelengths of light from the continuous wave excitation sources to the optical viewing region;
  illuminating each particle found in the sample stream in the viewing region with the excitation sources substantially simultaneously, said particle having elastic scattering properties, fluorescence or non-fluorescence emission properties, and dimension and density properties;
  directing light from the viewing region to a plurality of detectors to produce a plurality of signals;
  directing the signals from the detectors to a signal processor to substantially simultaneously measure the elastic scattering properties, the complex refractive index and the fluorescence or non-fluorescence of the particle substantially simultaneously and in substantially real time.

2. The method of claim 1, wherein the plurality of detectors comprises a plurality of detectors dedicated to detecting particle elastic scattering properties.

3. The method of claim 1, wherein the plurality of detectors comprises a plurality of detectors dedicated to detecting particle elastic scatter and at least one detector dedicated to detecting fluorescence.

4. The method of claim 1, wherein the plurality of continuous wave excitation sources are selected from the group consisting of lasers, light emitting diodes, and light emitting devices producing discrete particle excitation wavelength ranges.

5. The method of claim 4, wherein the lasers produce particle excitation ranges selected from the group consisting of from about 266 nm to about 300 nm; about 350 nm to about 430 nm; about 400 nm to about 430 nm and from about 600 nm to about 1500 nm.

6. The method of claim 4, wherein the excitation ranges are selected from the group consisting of from about 266 nm to about 280 nm, and from about 400 nm to about 415 nm, and from about 700 nm to about 1.5 µm.

7. The method of claim 1, wherein the particle is a biological particle.

8. The method of claim 7, wherein the biological particle comprises fluorophores or chromophores.

9. The method of claim 8, wherein the fluorophores are selected from the group consisting of amino acids, NADH, flavins and chlorophylls.

10. The method of claim 1, wherein the particle is a non-biological particle.

11. The method of claim 1, wherein at least two detectors are used to measure elastic scatter and complex refractive index and at least one detector is used to measure fluorescence.

12. The method of claim 1, wherein at least two detectors are used to measure elastic scatter and complex refractive index.

13. The method of claim 1, wherein the particle is inspected according to a dimensional feature space greater than or equal to a seven dimensional feature space.

14. The method of claim 4, wherein the continuous wave excitation sources comprise three lasers.

15. The method of claim 4, wherein the continuous wave excitation sources comprise two lasers.

16. The method of claim 1, wherein the particle is airborne.

17. A method for detecting and classifying a particle comprising the steps of:
  providing and directing a sample stream containing particles to an optical viewing region;
  providing a continuous wave excitation sources, said continuous wave source emitting a discrete wavelength;
  providing a pulsed wave excitation source, said pulsed wave excitation source emitting a discrete wavelength;
  providing at least one nonlinear crystal for generating second and third harmonic wavelength generation;
  directing a plurality of discrete wavelengths of light from the continuous wave excitation source and the pulsed wave excitation source to the optical viewing region;
  illuminating each particle found in the sample stream in the viewing region with the excitation sources substantially simultaneously, said particle having elastic scattering properties, fluorescence or non-fluorescence emission properties, and dimension and density properties;
  directing light from the viewing region to a plurality of detectors to produce a plurality of signals;
  directing the signals from the detectors to a signal processor to substantially simultaneously measure the elastic scattering properties, the complex refractive index and the fluorescence or non-fluorescence of the particle substantially simultaneously in substantially real time.

18. The method of claim 17, wherein three detectors are used to measure elastic scatter and complex refractive index and at least one detector is used to measure fluorescence.

19. The method of claim 1, wherein the laser produces a plurality of excitation wavelengths, at least one excitation wavelength of which operates in a continuous manner to provide a triggering mechanism for a detection mode.

20. The method of claim 1, wherein each excitation source provides a different excitation wavelength, with each wavelength is optically aligned along the same axis orthogonal to an optical viewing region.

21. The method of claim 1, wherein each excitation source provides three different excitation wavelengths, with two of the wavelengths aligned along the same axis orthogonal to a particle detection space, and with the third wavelength separated at a defined distance from the other two wavelengths.

22. The method of claim 1, wherein each excitation source provides three different excitation wavelength, with all three wavelengths separated from each other at a defined distance.

23. The method of claim 1, wherein each excitation source provides two different excitation wavelengths, with one of the two wavelengths aligned along the same axis orthogonal to a particle detection space, and with one of the two wavelengths separated at a defined distance from the other wavelengths.

24. The method of claim 4, wherein the excitation source produces a beam conditioned to have line thickness of from about 5 to about 300 microns.

25. The method of claim 1, further comprising the steps of:
directing a sample of air to the optical viewing region from an environment selected from the group consisting of an exterior environment and an interior environment.

26. The method of claim 1, further comprising the steps of:
directing a sample of air to the optical viewing region from an environment selected from the group consisting of: a battlefield, a hospital, a mailroom, an industrial facility, a vehicle compartment; a building interior, and an air stream with and without communication with an HVAC system.

27. The method of claim 17, wherein the particle is airborne.

28. An apparatus for detecting and classifying a single particle from a sample comprising:
a plurality of continuous wave excitation sources, each source emitting a discrete wavelength, the wavelengths directed through an optical viewing region;
a plurality of detectors to receive the wavelengths directed through the optical viewing region and produce a plurality of signals; and
a signal processor in communication with each detector to receive the signal from the detector to substantially simultaneously measure the elastic scattering properties, the complex refractive index and the fluorescence or non-fluorescence of the particle substantially simultaneously and in substantially real-time.

29. The apparatus of claim 28, wherein the plurality of detectors comprises a plurality of detectors dedicated to detecting particle elastic scattering properties.

30. The apparatus of claim 28, wherein the plurality of detectors comprises a plurality of detectors dedicated to detecting particle elastic scatter and at least one detector dedicated to detecting particle fluorescence.

31. The apparatus of claim 28, wherein the plurality of continuous wave excitation sources are selected from the group consisting of lasers, light emitting diodes, and light emitting devices producing discrete particle excitation wavelength ranges.

32. The apparatus of claim 31, wherein the lasers produce particle excitation ranges selected from the group consisting of from about 266 nm to about 300 nm; about 350 nm to about 430 nm; about 400 nm to about 430 nm; and from about 600 nm to about 1500 nm.

33. The apparatus of claim 28, wherein the particle is a biological particle.

34. The apparatus of claim 33, wherein the biological particle comprises fluorophores or chromophores.

35. The apparatus of claim 34, wherein the fluorophores are selected from the group consisting of amino acids, NADH, flavins and chlorophylls.

36. The apparatus of claim 28, wherein the particle is a non-biological particle.

37. The apparatus of claim 28, wherein at least two detectors are used to measure elastic scatter and complex refractive index and at least one detector is used to measure fluorescence.

38. The apparatus of claim 28, wherein at least two detectors are used to substantially simultaneously measure elastic scatter and complex refractive index.

39. The apparatus of claim 28, wherein the particle is inspected according to a dimensional feature space greater than or equal to a seven dimensional feature space.

40. The apparatus of claim 28, wherein the continuous wave excitation sources comprise three lasers.

41. The apparatus of claim 28, wherein the continuous wave excitation sources comprise two lasers.

42. The apparatus of claim 28, wherein the excitation source produces a beam conditioned to have a line thickness of from about 5 to about 300 microns.

43. The apparatus of claim 28, wherein the particle is airborne.

44. An apparatus for detecting and classifying a single particle from a sample comprising:
a continuous wave excitation sources, said continuous wave excitation source emitting a discrete wavelength, the wavelength directed through an optical viewing region;
a pulsed wave excitation source, said pulsed wave excitation source emitting a discrete wavelength;
at least one nonlinear crystal for generating second and thirds harmonic wavelengths;
a plurality of detectors to receive the wavelengths directed through the optical viewing region and produce a plurality of signals; and
a signal processor in communication with each detector to receive the signal from the detector to substantially simultaneously measure the elastic scattering properties, the complex refractive index and the fluorescence or non-fluorescence of the particle substantially simultaneously and in substantially real time.

45. The apparatus of claim 44, wherein three detectors are used to measure elastic scatter and complex refractive index and at least one detector is used to measure fluorescence.

46. The apparatus of claim 44, wherein the continuous wave laser operates in a continuous manner to provide a triggering mechanism for a detection mode.

47. The apparatus of claim 44, wherein each excitation source provides a different excitation wavelength, with each wavelength optically aligned along the same axis orthogonal to an optical viewing region.

48. The apparatus of claim 44, wherein each excitation source provides three different excitation wavelength, with two of the wavelengths aligned along the same axis orthogonal to a particle detection space, and with the third wavelength separated at a defined distance from the other two wavelengths.

49. The apparatus of claim 44, wherein each excitation source provides three different excitation wavelength, with all three wavelengths optically aligned with all three wavelengths separated from each other at a defined distance.

50. The apparatus of claim 44, wherein each excitation source provides two different excitation wavelength, with one of the two wavelengths aligned along the same axis orthogonal to a particle detection space, and with one of the two wavelength separated at a defined distance from the other wavelength.

51. The apparatus of claim 44, wherein the excitation source produces a beam conditioned to have a line thickness of from about 5 to about 300 microns.

52. The apparatus of claim 44, further comprising detectors for detecting fluorescence having a wide angle collection configuration of about $4\pi$ steradians.

53. A vehicle comprising the apparatus of claim 28.

54. A vehicle comprising the apparatus of claim 44.

55. A building comprising the apparatus of claim 28.

56. A building comprising the apparatus of claim 44.

57. A system for detecting biological and non-biological particles comprising the apparatus of claim 26.

58. A system for detecting biological and non-biological particles comprising the apparatus of claim 41.

* * * * *

UNITED STATES PATENT AND TRADEMARK OFFICE
CERTIFICATE OF CORRECTION

| | | |
|---|---|---|
| PATENT NO. | : 7,106,442 B2 | Page 1 of 1 |
| APPLICATION NO. | : 10/834537 | |
| DATED | : September 12, 2006 | |
| INVENTOR(S) | : Silcott | |

It is certified that error appears in the above-identified patent and that said Letters Patent is hereby corrected as shown below:

On the Title page of the issued patent, please include the priority data, which includes:

--Priority Application – U.S. Provisional Application No. 60/466,042, filed on April 29, 2003.--

In the "Cross-Reference" Section, please replace the paragraph as follows:

--This application claims the benefit of U.S. Provisional Patent Application No. 60/466,042, filed April 29, 2003.--

Signed and Sealed this

Eighth Day of December, 2009

David J. Kappos
*Director of the United States Patent and Trademark Office*